United States Patent
Janik

(10) Patent No.: US 9,910,191 B2
(45) Date of Patent: Mar. 6, 2018

(54) MAGNIFICATION LOUPE WITH ASPHERICAL LENSES

(75) Inventor: Steffen Janik, Au (CH)

(73) Assignee: FORSTGARTEN INTERNATIONAL HOLDING GMBH, St. Gallen (CH)

( * ) Notice: Subject to any disclaimer, the term of this patent is extended or adjusted under 35 U.S.C. 154(b) by 616 days.

(21) Appl. No.: 12/531,301

(22) PCT Filed: Feb. 26, 2008

(86) PCT No.: PCT/EP2008/001521
§ 371 (c)(1),
(2), (4) Date: Apr. 30, 2010

(87) PCT Pub. No.: WO2008/110264
PCT Pub. Date: Sep. 18, 2008

(65) Prior Publication Data
US 2010/0214656 A1    Aug. 26, 2010

Related U.S. Application Data

(60) Provisional application No. 60/894,941, filed on Mar. 15, 2007.

(51) Int. Cl.
*G02B 23/00*    (2006.01)
*G02B 3/04*    (2006.01)
(Continued)

(52) U.S. Cl.
CPC .............. *G02B 3/04* (2013.01); *A61B 90/36* (2016.02); *G02B 25/004* (2013.01);
(Continued)

(58) Field of Classification Search
CPC .......... G02B 1/041; G02B 1/043; G02B 3/00; G02B 3/02; G02B 7/00; G02B 7/02;
(Continued)

(56) References Cited

U.S. PATENT DOCUMENTS 2,024,322 A * 12/1935 Wittig ........................... 359/411
2,043,840 A *  6/1936 Singer .................... G02C 7/105
                                                         351/159.63
(Continued)

FOREIGN PATENT DOCUMENTS

DE      26 32 263    *  1/1978 .................... 359/407
DE     19860432 A1     7/2000
(Continued)

OTHER PUBLICATIONS

International Preliminary Report on Patentability dated Sep. 15, 2009 in International Application No. PCT/EP2008/001521.
(Continued)

*Primary Examiner* — Thong Nguyen
(74) *Attorney, Agent, or Firm* — Davé Law Group LLC; Raj S. Dave

(57) ABSTRACT

The present invention relates to optical instruments, in particular to magnification loupes, stereo-magnification loupes and magnification viewers, such as those worn by dentists and surgeons. The objective lens of the optical instrument is protected from mechanical and/or chemical damage.

15 Claims, 4 Drawing Sheets

(51) Int. Cl.
*G02B 25/00* (2006.01)
*A61B 90/00* (2016.01)
*G02B 7/00* (2006.01)

(52) U.S. Cl.
CPC .... *G02B 25/008* (2013.01); *A61B 2090/3616* (2016.02); *G02B 7/002* (2013.01)

(58) Field of Classification Search
CPC ........ G02B 7/021; G02B 7/022; G02B 7/025; G02B 13/00; G02B 13/0015; G02B 13/002; G02B 13/0055; G02B 23/00; G02B 23/14; G02B 23/16; G02B 23/2461; G02B 23/2476; G02B 25/00; G02B 25/002; G02B 25/02; G02B 3/04; G02B 25/004; G02B 25/008
USPC .......................... 359/399–431, 642, 800–819
See application file for complete search history.

(56) References Cited

U.S. PATENT DOCUMENTS

| | | | | |
|---|---|---|---|---|
| 2,459,021 | A * | 1/1949 | Frommer | G02B 25/004 351/158 |
| 2,777,129 | A * | 1/1957 | Hummel | 2/8.1 |
| 3,244,072 | A * | 4/1966 | Dowling et al. | G02B 23/18 359/412 |
| 3,273,456 | A * | 9/1966 | Feinbloom | 359/481 |
| 4,094,585 | A | 6/1978 | Betensky | |
| 4,196,966 | A | 4/1980 | Malis | |
| 4,274,128 | A | 6/1981 | Malis | |
| 4,523,808 | A * | 6/1985 | Miller et al. | 359/481 |
| 4,807,987 | A | 2/1989 | Bastable et al. | |
| 4,834,525 | A * | 5/1989 | Vansaghi | 351/158 |
| 4,865,438 | A * | 9/1989 | Wada | 351/158 |
| 5,076,682 | A | 12/1991 | Pasfield | |
| 5,162,824 | A * | 11/1992 | Klemka | G02C 7/088 351/158 |
| 5,266,977 | A * | 11/1993 | Linden | 351/47 |
| 5,381,263 | A * | 1/1995 | Nowak et al. | 359/411 |
| 5,428,474 | A * | 6/1995 | Murphy | 359/361 |
| 5,526,178 | A | 6/1996 | Goldstein et al. | |
| 5,680,194 | A * | 10/1997 | Pasfield | G02B 7/002 351/158 |
| 5,704,063 | A * | 1/1998 | Tilden | 2/9 |
| 5,905,478 | A | 5/1999 | Hildebrand et al. | |
| 6,061,189 | A | 5/2000 | Caplan et al. | |
| 6,157,501 | A * | 12/2000 | Sato | G02B 7/02 359/811 |
| 6,172,808 | B1 * | 1/2001 | Foreman et al. | 359/481 |
| 6,437,927 | B1 | 8/2002 | Shafer | |
| 6,996,846 | B1 * | 2/2006 | Karapetyan | 2/9 |
| RE39,162 | E | 7/2006 | Caplan et al. | |
| D588,618 | S * | 3/2009 | Janik | D16/135 |
| 2003/0016949 | A1 | 9/2003 | Porter et al. | |
| 2004/0070823 | A1 * | 4/2004 | Radna | 359/407 |
| 2004/0165278 | A1 | 8/2004 | Cahall | |
| 2006/0103924 | A1 * | 5/2006 | Katz | 359/399 |
| 2006/0192917 | A1 * | 8/2006 | Chang | 351/57 |
| 2006/0268220 | A1 * | 11/2006 | Hogan | 351/47 |

FOREIGN PATENT DOCUMENTS

| | | |
|---|---|---|
| EP | 0453755 A1 | 10/1991 |
| JP | 53-135123 A | 11/1978 |
| JP | 54-14761 A | 2/1979 |
| JP | 55-52122 A | 4/1980 |
| JP | 55-116314 A | 9/1980 |
| JP | 2003-532137 A | 10/2003 |
| JP | 2005-018068 A | 1/2005 |
| JP | 2005-107250 A | 4/2005 |
| JP | 2007-47319 A | 2/2007 |
| WO | 99/03010 A1 | 1/1999 |
| WO | 01/81973 A1 | 11/2001 |

OTHER PUBLICATIONS

International Search Report and Written Opinion dated Jul. 7, 2008 in International Application No. PCT/EP2008/001521.

* cited by examiner

MAGNIFICATION LOUPE WITH ASPHERICAL LENSES

This application is a National Stage of International Application No. PCT/EP2008/001521, filed Feb. 26, 2008, which claims priority to U.S. Provisional Patent Application No. 60/894,941. The contents of both applications are incorporated herein by reference in their entireties.

FIELD OF THE INVENTION

The present invention relates to optical instruments, in particular to magnification loupes, stereo-magnification loupes and magnification viewers, such as those worn by dentists and surgeons.

BACKGROUND OF THE INVENTION

Magnification viewers are well known in the art and generally comprise one or more optical loupes coupled to eyeglass frames or headbands. Such magnification viewers are often worn by physicians for extended periods of time during clinical procedures so as to provide clarity of view and a magnified image of the body part of interest, while avoiding a "hunched over position" that can result in debilitating neck and back strain, and which can consequently have an adverse effect on the success of an operation. By permitting the physician to operate at a greater working distance from the patient, magnification viewers also reduce the physician's exposure to potential contamination from aerosols.

Since physicians use magnification viewers during surgery and other procedures requiring manual precision over extended periods of time, it is important that they be lightweight, comfortable, and provide good clarity and a wide field of vision while providing high resolution.

The optical loupes of clinical magnification viewers are often made according to the Galilean telescope design, having a single objective lens and a single eyepiece lens. Galilean telescopes are characterized by relatively narrow fields of view that are mainly limited by the diameter of the objective lens. The basic Galilean design, however, produces substantial chromatic aberration ("colouring") and lack "edge to edge" clarity. Thus, image quality is poor.

The chromatic aberration of the basic Galilean design may partially be overcome by combining convex and concave lenses with different refractive indexes. However, this addition of further lenses increases the weight of the loupe and the magnification viewer.

Another well known loupe design is the so-called Keplerian design which uses prisms to enhance "edge to edge" clarity and to provide higher magnification values than the basic Galilean design. The additional prisms, however, add to the weight of the individual loupe element and, thus, of the magnification viewer.

Aspherical lenses have long been known in the art and exhibit much less chromatic aberration and provide superior "edge to edge" clarity as compared to the conventional lenses typically used in the Galilean design. Aspherical glass lenses, however, are even nowadays difficult to grind and polish and are thus expensive. Aspherical plastic lenses can be produced by injection moulding and are, thus, much cheaper in production than aspherical glass lenses as soon as a casting mould is available. Plastic lenses, however, suffer from other disadvantages, namely that they are prone to mechanical, heat or chemical damage. In other words they are easily scratched, scuffed, affected by organic solvents or otherwise damaged, especially during cleaning and have been perceived as not suitable to be used the harsh clinical environment requiring aseptic conditions. Accordingly, aspherical plastic lenses have not been used in clinical settings as of yet.

In summary, a need exists for improved magnification loupes and magnification viewers, particularly for use in clinical applications, which are light-weight and provide good edge to edge clarity.

SUMMARY OF THE INVENTION

In a first aspect the present invention relates to a magnification loupe, comprising: (a) a housing having a first end with a first aperture for supporting an eyepiece lens system and a second end with a second aperture for supporting an objective lens; (b) an eyepiece lens system disposed in said first end of said housing; and (c) an objective lens system disposed in said second end of said housing, wherein said objective lens system comprises at least one aspherical plastic lens protected from mechanical and/or chemical damage.

In a second aspect the present invention relates to a stereo-magnification loupe comprising two magnification loupes according to the first aspect of the invention operatively coupled in a distance to provide a magnified stereo view to a user.

In a third aspect the present invention relates to a magnification viewer comprising a user wearable device and at least one magnification loupe according to the first aspect of the invention or a stereo-magnification loupe according to the second aspect of the invention operatively coupled to said user wearable device.

DETAILED DESCRIPTION

Definitions

Figure 1:
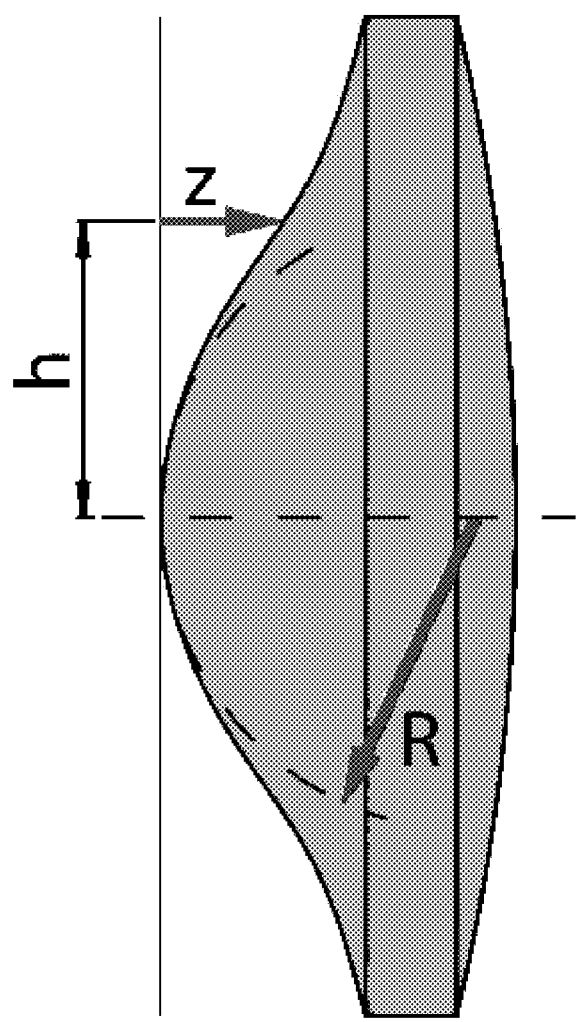
FIG. 1 is a side view of an aspherical lens showing the parameters with which the form of the lens can be described.
Figure 2:
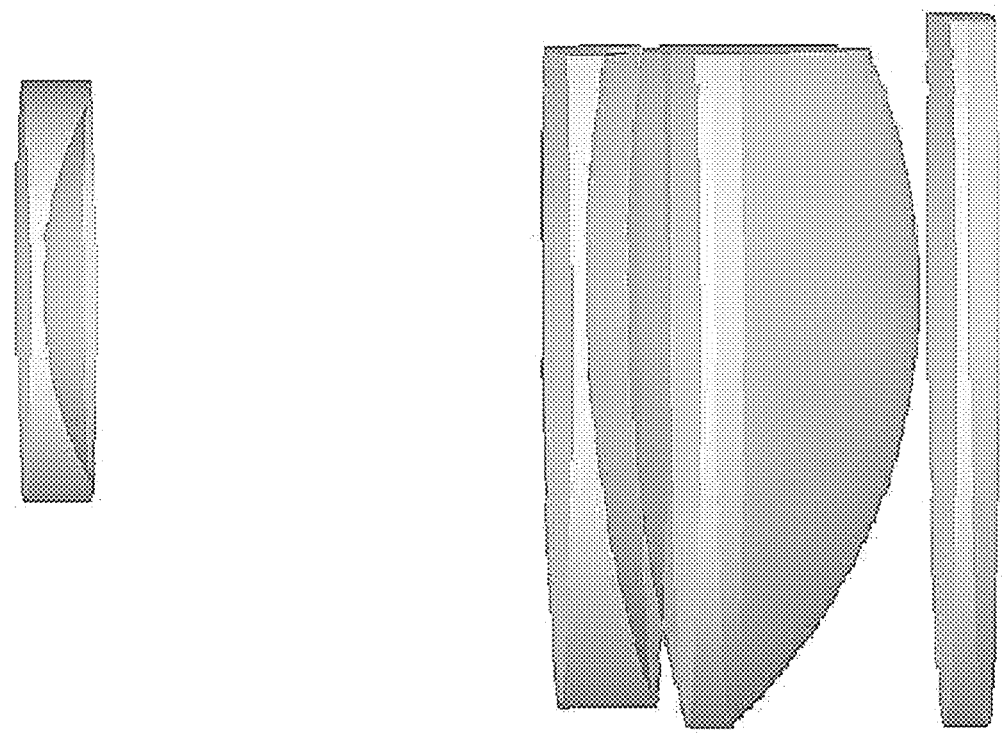
FIG. 2 is a side view of the lens arrangement of the magnification loupe according to one embodiment of the invention. The eyepiece lens system to the left consists of one single lens. The objective lens system to the right consists of three lenses (from left to right): a lens which may be made of plastic or glass; an aspherical plastic lens; and a protective glass lens.

Before the present invention is described in detail below, it is to be understood that this invention is not limited to the particular methodology, designs and materials described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, is hereby incorporated by reference in its entirety. Nothing herein is to be construed as an admission that the invention is not entitled to antedate such disclosure by virtue of prior invention.

A "lens" within the meaning of the present invention may be "spherical" or "aspherical". A "spherical lens" has front and back surfaces which can be imagined to be part of a surface of a sphere. The front surface and the back surface of a "spherical" lens, thus, may be independently from each other convex or concave or may also be planar. Additionally, the lens may be diffractive. Accordingly, a preferred lens usable in the eyepiece and/or the objective lens system of the present invention is a double convex lens, a meniscus lens, an aspheric lens, a kino-form-corrected aspheric double convex lens, a kino-form-corrected aspheric meniscus, a flat-field apochromatic single-element simple microscope lens, a plano/spheric convex lens, a plano/aspheric convex lens, a plano/diffractive lens, a plano/diffractive-spheric convex lens, a plano/diffractive-aspheric convex lens, a diffractive plano/spheric convex lens, a diffractive plano/aspheric convex lens, a double convex spheric/spheric lens, a double convex spheric/aspheric lens, a double convex aspheric/aspheric lens, a double convex diffractive-spheric/aspheric lens, a double convex spheric/diffractive-aspheric lens, a double convex aspheric/diffractive-aspheric lens, a double convex diffractive-aspheric/diffractive-aspheric lens, a spheric/spheric meniscus lens, a spheric/aspheric meniscus lens, an aspheric/aspheric meniscus lens, a diffractive/diffractive meniscus lens, a diffractive-spheric/spheric meniscus lens, a diffractive-spheric/diffractive-spheric meniscus lens, a diffractive-spheric/aspheric meniscus lens, a spheric/diffractive-aspheric meniscus lens, an aspheric/diffractive-aspheric meniscus lens, and a diffractive-aspheric/diffractive-aspheric meniscus or a lens planar on both surfaces. In a preferred embodiment the lens is diffractive-aspheric. Accordingly, also a lens having neither convex nor concave surfaces, i.e. both the front surface and the back surface of the lens are planar, is considered to be a lens within the meaning of the present invention. In other words, also a pane of glass is considered a lens within the context of certain embodiments of the present invention. In one preferred embodiment, the protective lens of the eyepiece lens system has two planar surfaces, i.e. the protective lens may be a pane of glass or a disposable pane of plastic. In another preferred embodiment the protective lens is a glass lens or a disposable lens of plastic and has a shape suitable to change the focal point of the magnification loupe upon lateral movement along the optical axis of the magnification loupe. In this embodiment the lens is preferably configured to be rotated around the optical axis of the magnification loupe, allowing the user to adjust the focus of the magnification loupe with a twist of the protective glass lens. If the protective lens is disposable the housing is configured to allow easy removal of the protective lens. This may be achieved by providing a thread at the second end of the housing and a corresponding thread at the disposable lens allowing a twist-of removal or by providing a sliding connection secured with a flexible pin or ledge.

An "aspherical lens" has at least one surface which cannot be described as being a part of the surface of a sphere. "Aspherical lenses" may nevertheless exhibit rotational symmetry and their shape may be calculated as a conic section plus a higher order power series. In accordance with DIN ISO 10110-12 the form of an aspheric lens may be calculated according to the following formula I:

$$z = f(h) = \frac{h^2}{R\left(1 + \sqrt{1 - (1+k)\left(\frac{h}{R}\right)^2}\right)} + A_4 h^4 + A_6 h^6 \ldots \quad \text{Formula I}$$

wherein
z=versed sine
h=distance perpendicular to the axis
R=vertex radius
k=conic constant
$A_4, A_6, \ldots$ =aspherical parameters FIG. 1 shows a side view of an aspherical lens wherein the variables z, h, and R are indicated.

A "user wearable device" according to the present invention may be any device which when worn allows the user to view through a magnification loupe or a stereo-magnification loupe that are (is) mounted to the user wearable device. Typically, the user wearable device is worn on the head, such as a face shield, a headband or eyeglasses, but it is also contemplated that the user-wearable device may be worn around the neck or on the shoulders.

A "translucent element" according to the present invention primarily serves the purpose of providing the user further protection from, e.g. liquids, blood etc emanating from the field of operation, while providing the user with a wider filed of view. Preferably, the translucent element is a lens of eyeglasses worn by the user or the transparent pane of a face shield. In the case of eyeglasses, the lens may be a prescription lens.

The "housing" of the magnification loupe is preferably made of light-weight, durable plastic, e.g. polycarbonate (PC), polyamide (PA), polyimide (PI), polyetheretherketone (PEEK), polyphenylenesulfide (PPSE), epoxide resin (EP), unsaturated polyester (UP), phenol resin (PF), melamine resin (MF), cyanate ester (CA), polytetrafluoroethylene (PTFE) and mixtures thereof. To improve the mechanical properties of plastic material, it can be reinforced by introducing other materials, especially fibres from glass, coal, aramide, or metal fibres. The resulting compounds are especially suitable synthetic materials due to their hardness. Examples for especially suitable fibres are aramide fibres (AF), coal fibres (CF) and glass fibres (GF). The housing is preferably flattened on one side, preferably on the side of the loupe facing the top of the loupe. Thus, in a preferred embodiment of the magnification loupe and the stereo-magnification loupe of this invention the user is less impeded by the top part of the housing as with the standard magnification loupes having a circular design. Preferably, only the lenses of the objective lens system are plane on one side to allow the design of a flat or essentially flat top of the housing. Preferably, 10 to 60%, e.g. 10, 15, 20, 25, 30, 35, 40, 45, 50, 55, or 60%, more preferably 20 to 50% of the radius of the lens is cut away on one side of the lens. While the removal leads to a slight reduction of the field of view of the magnification loupe or stereo-magnification loupe of the present invention it leads to a marked increase in the field of view, once the user raises the eyes to look over the magnification loupe or stereo-magnification loupe.

The "aspheric plastic lens" can be made of any optical grade plastic known in the art, including polyurethane and polycarbonate, preferably high index polyurethane and polycarbonate.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Figure 3:
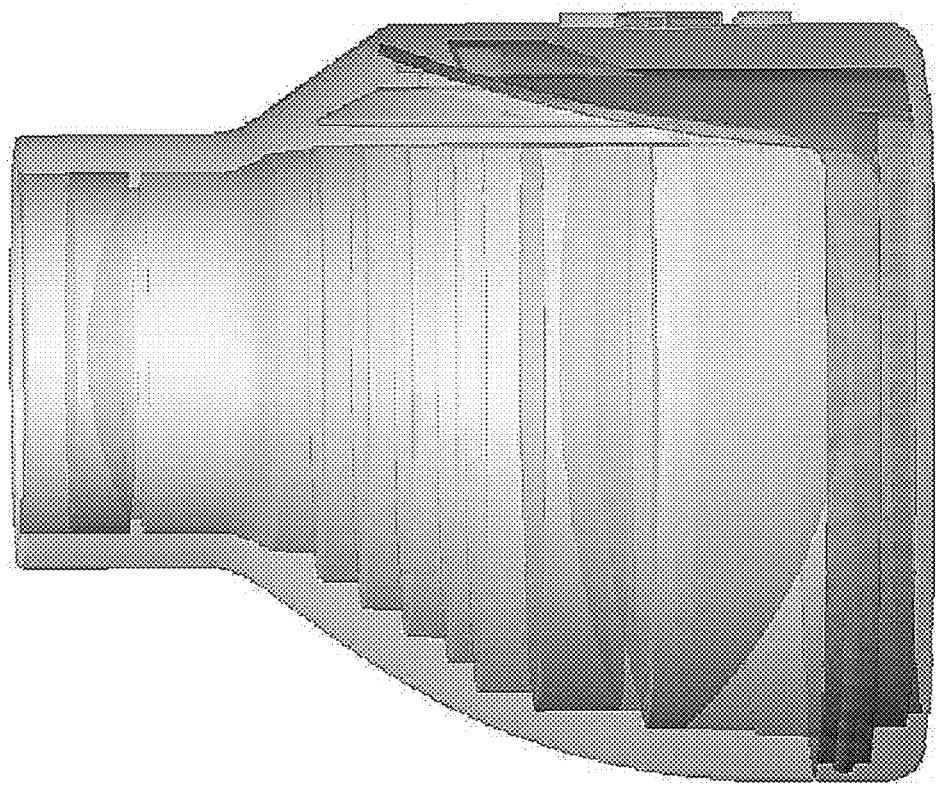
FIG. 3 is a side view of a translucent housing supporting the lens arrangement as shown in FIG. 2.
Figure 4:
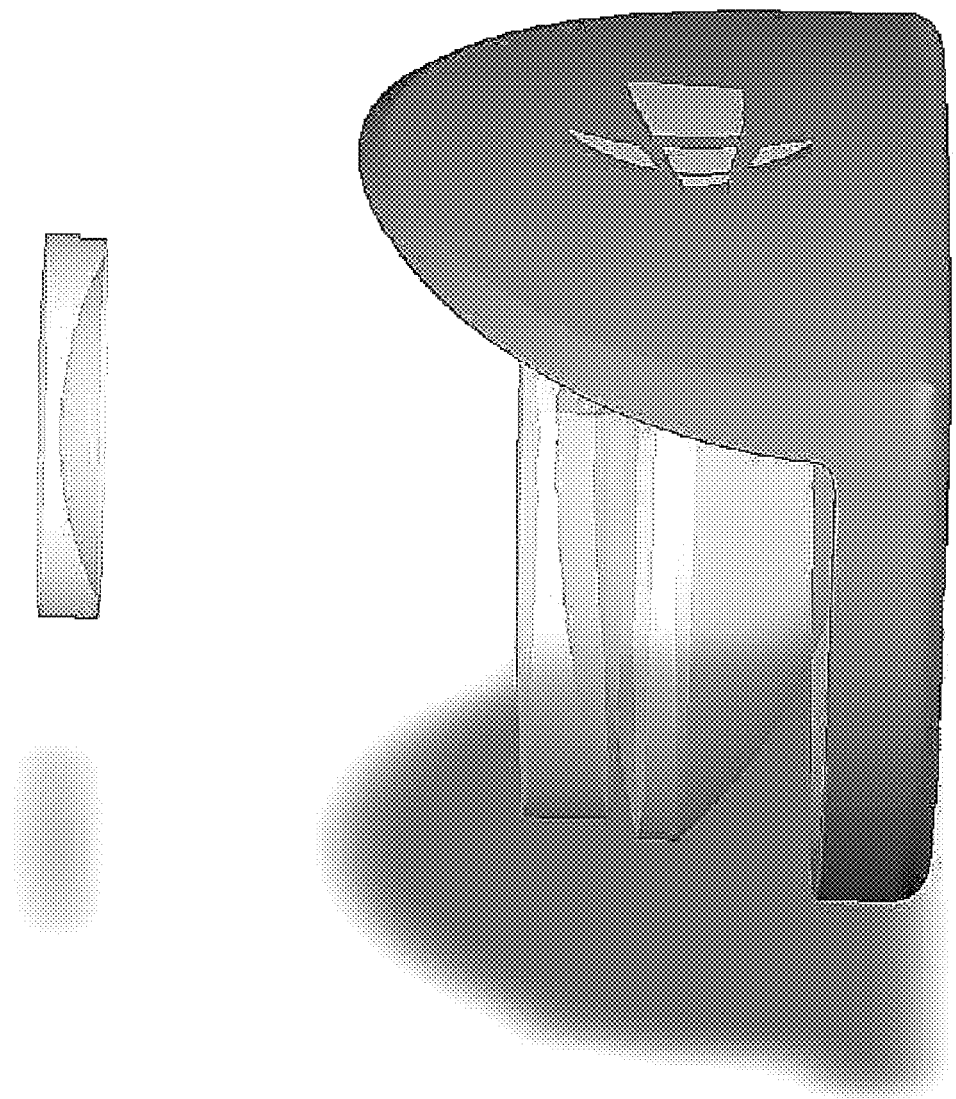
FIG. 4 is a perspective view of the lens arrangement of FIG. 2 also including the front part of the housing.

In a first aspect, the present invention provides a magnification loupe, comprising: (a) a housing having a first end with a first aperture for supporting an eyepiece lens system and a second end with a second aperture for supporting an objective lens; (b) an eyepiece lens system disposed in said first end of said housing; and (c) an objective lens system disposed in said second end of said housing, wherein said objective lens system comprises at least one aspherical plastic lens protected from mechanical and/or chemical damage. In preferred embodiments said at least one aspherical plastic lens or any other plastic lens disposed in the magnification loupe of the invention is produced by injection moulding. Preferably, the at least one aspherical plastic lens is protected by one or more of the following: (a) a protective layer covering the aspherical plastic lens at least on the side of the aspherical plastic lens which faces the second aperture of the housing, (b) at least one glass lens being part of the objective lens system, wherein said glass lens is positioned between the aspherical lens and the second aperture of the housing, and (c) at least one disposable plastic lens being positioned between the aspherical lens and the second aperture of the housing. Suitable protective layers are well known in the art and include, e.g. scratch resistant organo-silicate coatings, and inorganic-organic hybrid polymers (e.g. ORMOCER®), which may be synthesized via sol-gel processing. Typically the protective lens is positioned at the end of the housing, i.e. is positioned at the second aperture. The glass lens preferably is a pane of glass, which is positioned at the end of the second aperture (see FIG. 3). The disposable plastic lens is attached between the aspherical lens and the second aperture, e.g. at the second aperture in such that it can be easily removed and replaced by a scratch free and/or sterile plastic lens. It is further preferred that the aspherical plastic lens is diffractive, e.g. a plano/diffractive-aspheric convex lens, a diffractive plano/aspheric convex lens, a double convex diffractive-spheric/aspheric lens, a double convex spheric/diffractive-aspheric lens, a double convex aspheric/diffractive-aspheric lens, a double convex diffractive-aspheric/diffractive-aspheric lens, a diffractive-spheric/aspheric meniscus lens, a spheric/diffractive-aspheric meniscus lens, an aspheric/diffractive-aspheric meniscus lens, or a diffractive-aspheric/diffractive-aspheric meniscus lens.

In preferred embodiments of the magnification loupe of the invention, the objective lens system comprises 0, 1, 2 or 3 further lenses in addition to the at least one aspherical lens. In some embodiments, one or more lenses of said further lenses of the objective lens system are made of plastic. Any of this lens may be a diffractive aspherical lens.

In preferred embodiments of the magnification loupe of the invention, the eyepiece lens system consists of 1, 2, 3 or 4 lenses. In preferred embodiments one or more lenses of the eyepiece lens system is made of plastic. In preferred embodiments any of this lens may be a diffractive lens.

In the embodiment of the present invention using a protective glass lens it is particularly preferred that all other lenses of the objective lens system (and in some preferred embodiment also of the eyepiece lens system) but the protective lens are plastic lenses.

In preferred embodiments of the magnification loupe of the invention, the housing further comprises means for the fixation of a prism system, said means being positioned between the eyepiece lens system and the objective lens system, and wherein the magnification loupe further comprises a Keplerian prism system operatively fixed within the housing by said means for fixation. It is preferred that said Keplerian prism system consists of 2 prisms.

In preferred embodiments of the magnification loupe of the invention, the magnification loupe has a magnification in the range of 2 to 10, e.g. 2, 3, 4, 5, 6, 7, 8, 9, or 10.

Under operating condition is often necessary to provide a focused image very close to the face of the user. Accordingly, the magnification loupe of the present invention is preferably configured, i.e. using appropriate optical elements, which would be known to the skilled person, to provide a focused image already at a working distance of 25 cm. In general it is not required to configure the optical elements of the magnification loupe in such that it is capable of providing a focused image beyond a distance of 200 cm. Accordingly, it a preferred embodiment the working distance, i.e. the distances wherein a focused image may be provided is between 25 cm and 200 cm, e.g. 25, 30, 35, 40, 50, 60, 70, 80, 90, 100, 110, 120 or more cm. In some embodiments a focused image may also be provided over a distance from 25 cm to at least 200 cm. It is also contemplated that infinite focus is provided.

In a second aspect, the present invention provides a stereo-magnification loupe comprising two magnification loupes as defined throughout this specification operatively coupled in a distance to provide a magnified stereo view to a user. The two magnification loupes are preferably coupled to each other by a metal or plastic frame. Preferably the frame allows to adjust the distance between the two magnification loupes. The frame may be provided with means to attach the stereo-magnification loupe to a wearable device, e.g. a clip or screw system.

In a third aspect, the present invention provides a magnification viewer comprising a user wearable device and at least one magnification loupe as defined throughout this specification or a stereo-magnification loupe according to the second aspect of the present invention operatively coupled to said user wearable device. In preferred embodiments of the magnification viewer of the invention, the user wearable device comprises at least one translucent element. In some embodiments the housing of at least one magnification loupe is configured for mounting through said translucent element of the user wearable device. In some embodiments the housing of at least one magnification loupe is operatively fixed to said translucent element by means of an adhesive. In some embodiments the user wearable device comprises a frame, and the housing of at least one magnification loupe is configured to be mounted to the user wearable device by a mounting member secured to said frame of the user wearable device.

In preferred embodiments of the magnification viewer of the invention, the user wearable device is selected from the group consisting of (a) a face shield; (b) a headband; and (c) eyeglasses.

In especially preferred embodiments of the magnification viewer of the invention, the magnification viewer additionally comprises an illumination assembly. It is especially preferred that the illumination beam supplied by the illumination assembly corresponds as closely as possible to the user's line of vision, i.e. the illumination assembly should illuminate the patient or workpiece from a point as close to the user's eyes as possible (preferably from immediately between the eyes). Otherwise, the user's hands, arms or other objects may obstruct the light path and cast shadows on the patient or workpiece and increase the difficulty in viewing the patient or workpiece. Also, dentists and medical personnel often have a need to look into very small holes, such as holes drilled into teeth, and the interior of such holes generally cannot be viewed without direct illumination along the axis of the hole. If the illumination source is mounted near the user's eyes and emits a beam of illumination which is parallel to and very nearly coaxial with the user's line of sight, the chances for the creation of shadows is minimized. Additionally, such a mounting position ensures that the user will automatically illuminate any area the user views provided the user's head is directed toward that area.

In preferred embodiments, the illumination assembly may comprise one or more of the following: (a) a battery powered light source, (b) a stationary powered light source, (c) a fibre-optics light guide, and (d) a mirror.

In preferred embodiments of the magnification viewer of the invention, the illumination assembly comprises a plurality of light emitting diodes (LEDs) as described in PCT application WO 01/81973 A1 (Porter C. and Meysztowicz, S. M.; IATIA Instruments Pty Ltd.). In more preferred embodiments the light emitting diodes are energised by a battery which is preferably included in the illumination assembly or is attached to the magnification viewer but the battery may also be positioned external to the magnification viewer and may be connected to the light emitting diodes via an electricity cable. The light emitting diodes may alternatively be energised by an external stationary power source which is connected to the light emitting diodes via an electricity cable.

In further preferred embodiments of the magnification viewer of the invention, the illumination assembly is designed according to the illumination assembly shown in US reissued patent US RE39,162 E (Caplan, C. H. and Bushroe, F. N.; Kerr Corporation). In particular, the illumination assembly may comprise (i) a light guide having an output end and an input end, the input end being adapted for connection to a remote illumination source; (ii) a housing having a light guide opening and an illumination opening, the output end of the light guide extending within the housing and being aligned to illuminate the illumination opening; (iii) a lens mounted within the illumination opening; and (iv) attachment means for attaching, preferably for removably attaching, the housing to a user-wearable device In further preferred embodiments of the magnification viewer of the invention, the illumination assembly is a fibre optics illumination system comprising an adjustable lens and mirror system for projecting a spot of light to the surgical or dental site as described in U.S. Pat. No. 4,807,987 (Bastable, D. E. and Goldberg, T. I.).

The invention claimed is:

1. A magnification viewer comprising a user wearable device and at least one magnification loupe operatively coupled to said user wearable device, the magnification loupe comprising:
  (a) a housing having a first end with a first aperture for supporting an eyepiece lens system and a second end with a second aperture for supporting an objective lens system; wherein the housing is flattened on a top side of the magnification loupe;
  (b) the eyepiece lens system disposed in said first end of said housing; and
  (c) an objective lens system disposed in said second end of said housing, wherein said objective lens system comprises at least one aspherical lens, wherein 10 to 60% of a radius of the objective lens system is cut away on only one side of the objective lens system, thereby the objective lens system is plane on only one side such that there is a flat top of the housing.

2. The magnification viewer of claim 1, wherein the magnification loupe has a magnification in the range of 2.0 to 10.

3. The magnification viewer of claim 1, wherein the magnification loupe is configured to provide a working distance of at least 25 cm to 200 cm.

4. The magnification viewer of claim 1, wherein the user wearable device comprises at least one translucent element, and wherein the housing of at least one magnification loupe is configured for mounting through the translucent element of the user wearable device.

5. The magnification viewer of claim 1, wherein the user wearable device comprises at least one translucent element, and wherein said housing is operatively fixed to said translucent element by means of an adhesive.

6. The magnification viewer of claim 1, wherein the user wearable device comprises a frame, and wherein the housing of at least one magnification loupe is configured to be mounted to the user wearable device by a mounting member secured to said frame of the user wearable device.

7. The magnification viewer of claim 1, further comprising an illumination assembly.

8. The magnification viewer of claim 7, wherein the illumination assembly comprises one or more of the following:
  (a) a battery powered light source,
  (b) a stationary powered light source,
  (c) a fibre-optics light guide, and
  (d) a mirror.

9. The magnification viewer of claim 1, wherein the user wearable device does not include the eyeglass.

10. The magnification viewer of claim 1, wherein the user wearable device comprises of a face shield, which is not an eyeglass.

11. The magnification viewer of claim 10, wherein the face shield comprises a transparent pane.

12. The magnification viewer of claim 1, further comprising a translucent element configured to provide protection to the user from a liquid emanating from an area on which the user is viewing through the magnification viewer, while simultaneously providing the user with an overall field of view that is wider than the area.

13. The magnification view of claim 1, wherein the magnification viewer comprises a stereo-magnification loupe comprising two of said magnification loupes operatively coupled to provide a magnified stereo view to a user of the magnification viewer.

14. A magnification viewer comprising a user wearable device and at least one magnification loupe operatively coupled to said user wearable device, the magnification loupe comprising:
(a) a housing having a first end with a first aperture for supporting an eyepiece lens system and a second end with a second aperture for supporting an objective lens system;
wherein the housing is flattened on a top side of the magnification loupe;
(b) the eyepiece lens system disposed in said first end of said housing; and
(c) an objective lens system disposed in said second end of said housing, wherein said objective lens system comprises at least one aspherical lens, wherein 10 to 60% of a radius of the objective lens system is cut away on only one side of the objective lens system, thereby the objective lens system is plane on only one side such that there is a flat top of the housing,
wherein only a top side of lenses of the objective lens system is cut away.

15. A magnification viewer comprising a user wearable device and at least one magnification loupe operatively coupled to said user wearable device, the magnification loupe comprising:
(a) a housing having a first end with a first aperture for supporting an eyepiece lens system and a second end with a second aperture for supporting an objective lens system;
wherein the housing is flattened on a top side of the magnification loupe;
(b) the eyepiece lens system disposed in said first end of said housing; and
(c) an objective lens system disposed in said second end of said housing, wherein said objective lens system comprises at least one aspherical lens, wherein 10 to 60% of a radius of the objective lens system is cut away on only one side of the objective lens system, thereby the objective lens system is plane on only one side such that there is a flat top of the housing,
wherein lenses of the eyepiece lens system are circular.

* * * * *